US006478989B1

(12) United States Patent
Lin

(10) Patent No.: US 6,478,989 B1
(45) Date of Patent: Nov. 12, 2002

(54) AROMATIC SUBSTITUTED NAPHTHOPYRANS

(75) Inventor: Jibing Lin, Fremont, CA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 09/738,356

(22) Filed: Dec. 15, 2000

Related U.S. Application Data

(63) Continuation-in-part of application No. 09/507,276, filed on Feb. 18, 2000, now abandoned, which is a continuation-in-part of application No. 08/933,556, filed on Sep. 19, 1997, now abandoned.

(51) Int. Cl.[7] .............................. G02B 5/23; G02F 1/03; C07D 311/92; C07D 413/00; G02C 7/10
(52) U.S. Cl. ........................ 252/586; 351/163; 359/241; 544/150; 549/60; 549/389
(58) Field of Search ........................ 252/586; 544/150; 549/60, 389; 359/241; 351/163

(56) References Cited

U.S. PATENT DOCUMENTS

| | | | |
|---|---|---|---|
| 3,361,706 A | 1/1968 | Meriweather et al. ........ 260/39 |
| 3,562,172 A | 2/1971 | Ono et al. ................... 252/300 |
| 3,567,605 A | 3/1971 | Becker ....................... 204/158 |
| 3,578,602 A | 5/1971 | Ono et al. ................... 252/300 |
| 3,627,690 A | 12/1971 | Casella et al. .............. 252/300 |
| 4,215,010 A | 7/1980 | Hovey et al. ............... 252/300 |
| 4,342,668 A | 8/1982 | Hovey et al. ............... 252/586 |
| 4,360,653 A | 11/1982 | Stevens et al. ............. 526/301 |
| 4,816,584 A | 3/1989 | Kwak et al. .................... 544/71 |
| 4,818,096 A | 4/1989 | Heller et al. ................ 351/163 |
| 4,826,977 A | 5/1989 | Heller et al. .................. 544/70 |
| 4,880,667 A | 11/1989 | Welch ........................ 427/160 |
| 4,931,219 A | 6/1990 | Kwiatkowski et al. ...... 252/586 |
| 4,931,220 A | 6/1990 | Haynes et al. .............. 252/586 |
| 4,931,221 A | 6/1990 | Heller ........................ 252/586 |
| 4,980,089 A | 12/1990 | Heller ........................... 544/70 |
| 4,994,208 A | 2/1991 | McBain et al. ............. 252/586 |
| 5,066,818 A | 11/1991 | Van Gemert et al. ....... 549/389 |
| 5,200,116 A | 4/1993 | Heller ........................ 252/586 |
| 5,200,483 A | 4/1993 | Selvig ........................ 526/301 |
| 5,238,981 A | 8/1993 | Knowles ..................... 524/110 |
| 5,274,132 A | 12/1993 | Van Gemert ................ 549/389 |
| 5,373,033 A | 12/1994 | Toh et al. ..................... 822/96 |
| 5,384,077 A | 1/1995 | Knowles ..................... 252/586 |
| 5,405,958 A | 4/1995 | Van Gemert ................. 544/71 |
| 5,429,774 A | 7/1995 | Kumar ........................ 252/586 |
| 5,458,814 A | 10/1995 | Kumar et al. ............... 252/586 |
| 5,466,398 A | 11/1995 | Van Gemert et al. ....... 252/586 |
| 5,475,074 A | 12/1995 | Matuoka et al. ............ 526/336 |
| 5,514,817 A | 5/1996 | Knowles ..................... 549/384 |
| 5,552,090 A | 9/1996 | Van Gemert et al. ....... 252/586 |
| 5,552,091 A | 9/1996 | Kumar ........................ 252/586 |
| 5,565,147 A | 10/1996 | Knowles et al. ............ 252/586 |
| 5,573,712 A | 11/1996 | Kumar et al. ............... 252/586 |
| 5,578,252 A | 11/1996 | Van Gemert et al. ....... 252/586 |
| 5,645,767 A | 7/1997 | Van Gemert ................ 252/586 |
| 5,658,501 A | 8/1997 | Kumar et al. ............... 252/586 |
| 5,753,146 A | 5/1998 | Van Gemert et al. ....... 252/586 |
| 5,936,016 A | 8/1999 | Lareginie et al. ............. 524/94 |
| 6,153,126 A | 11/2000 | Kumar ........................ 252/586 |
| 6,337,409 B1 * | 1/2002 | Hughes et al. .............. 549/389 |
| 6,340,766 B1 * | 1/2002 | Lin ............................. 549/389 |
| 6,348,604 B1 * | 2/2002 | Nelson et al. .............. 549/389 |
| 6,353,102 B1 * | 3/2002 | Kumar ........................ 544/60 |
| 6,398,987 B1 * | 6/2002 | Breyne et al. .............. 252/586 |
| 6,399,791 B1 * | 6/2002 | Breyne et al. .............. 549/389 |

OTHER PUBLICATIONS

Olah et al., *Friedel–Crafts and Related Reactions*, Interscience Publishers, vol. 3, Chapter XXXI ("Aromatic Ketone Synthesis"), pp 1–8, 1964.

Ishihara et al., "Regioselective Friedel–Crafts Acylation of 1,2,3,4–Tetrahydroquinoline and Related Nitrogen Heterocycles: Effect on NH Protective Groups and Ring Size", J. Chem. Soc. Perkins Trans. 1, 1992, pp 3401–3406.

Sakamoto et al., "A Facile Synthesis of Ethynyl–Substituted Six–Membered N–Heteroaromatic Compounds", Synthesis, 1983, pp 312–314.

Takahashi et al., "A Convenient Synthesis of Ethynylarenes and Diethynylarenes", Synthesis, 1980, pp 627–630.

Bao et al., "Synthesis, Resolution and Determination of Absolute Configuration of a Vaulted 2,2'–Binaphthol and a Vaulted 3,3'–Biphenanthrol (VAPOL)", J. Am. Chem. Soc., vol. 118, No. 14, 1996, pp 3392–3405.

B. Van Gemert et al., "Naphthopyrans, Structural Features and Photochromic Properties", *Mol. Cryst. Liq. Cryst.*, 1997, vol. 297, pp 131–138.

* cited by examiner

Primary Examiner—Deborah C. Lambkin
(74) Attorney, Agent, or Firm—Frank P. Mallak

(57) ABSTRACT

Described are photochromic 2H-naphtho[1,2-b]pyrans characterized by having an aromatic substituent in the 5 position. The aromatic group at 5-position of the naphthopyran is a substituted or unsubstituted aryl group or other substituted or unsubstituted aromatic group. These compounds may be represented by the following graphic formula:

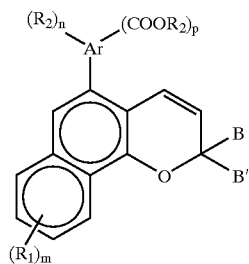

Also described are polymeric organic host materials that contain or that are coated with such compounds.

22 Claims, No Drawings

AROMATIC SUBSTITUTED NAPHTHOPYRANS

CROSS REFERENCE TO RELATED APPLICATIONS

This application is a continuation-in part of U.S. application Ser. No. 09/507,276, filed Feb. 18, 2000, abandoned, which is a continuation-in-part of U.S. application Ser. No. 08/933,556, filed Sep. 19, 1997, now abandoned.

DESCRIPTION OF THE INVENTION

The present invention relates to substituted 2H-naphtho [1,2-b]pyran compounds. More particularly, this invention relates to novel photochromic aromatic substituted naphthopyran compounds and to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1, 2-b]pyrans without the aforementioned additives ranges from several hours to many days to reach complete reversion.

U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions. U.S. Pat. No. 5,645,767 describes novel photochromic indeno-fused 2H-naphtho[1,2-b]pyran compounds, the 2,1-positions of the indeno group being fused to the f side of the naphthopyran.

The following four patents disclose related photochromic 2H-naphtho[1, 2-b]pyran compounds with certain substituents at the 2 position and certain aromatic substituents at the 5 position. U.S. Pat. No. 4,826,977 discloses naphthopyrans having an adamantane group at the 2 position, a phenyl or substituted phenyl group or a 5- or 6-membered heteroaromatic group at the 5 position. U.S. Pat. No. 4,931,221 discloses naphthopyrans having two cyclopropyl groups at the 2 position, and a phenyl or substituted phenyl group at the 5 position. U.S. Pat. No. 4,980,089 describes naphthopyrans having a norcamphor group or a tricyclodecane group at the 2 position, and a furyl group, thienyl group or phenyl or substituted phenyl group at the 5 position. U.S. Pat. No. 5,200,116 describes naphthopyrans having a cyclopropyl group along with a phenyl or substituted phenyl group, thienyl, benzothienyl group, or furyl or benzofuryl group at the 2 position and a phenyl or substituted phenyl group at the 5 position. The substituents of the 5 position phenyl groups disclosed in these four patents are $C_1$–$C_4$ alkyl, $C_1$–$C_4$ alkoxy, chloro or bromo.

U.S. Pat. No. 5,458,814 discloses photochromic 2H-naphtho[1,2-b]pyran compounds having certain substituents at the number 5 and 6 carbon atoms of the naphtho portion of the naphthopyran, and at the 2-position of the pyran ring. These compounds have an acceptable fade rate in addition to a high activated intensity and a high coloration rate.

The present invention relates to a naphthopyran of 2H-naphtho[1,2-b]pyran structure characterized by having and aromatic substituent in the 5 position. The compounds also have substituents at the 2 position of the pyran ring. The aromatic group at the 5-position of the naphthopyran is a substituted or unsubstituted phenyl or naphthyl group or other substituted or unsubstituted heteroaromatic group. It has unexpectedly been discovered that the compounds of the present invention are faster to fade than 2H-naphthopyrans having similar photochromic properties that are unsubstituted or have an aromatic substituent in the 5 position and a different substituent in the 6 position.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-à-vis, glass lenses. Moreover, photochromic transparencies for vehicles, such as cars and airplanes, have been of interest because of the potential safety features that such transparencies offer.

In accordance with the present invention, it has now been discovered that 2H-naphtho[1,2-b]pyrans characterized by having in the 5 position, a group —Ar($R_2$)$_n$(COOR$_3$)$_p$, that produce an activated yellow-orange color may be prepared. These compounds may be described as naphthopyrans having at the number 5 carbon atom of the naphthopyran a substituted or unsubstituted phenyl or naphthyl group or another substituted or unsubstituted heteroaromatic substituent, and substituents at the 2 position of the pyran ring. Substituents may also be present at the number 7, 8, 9 or 10 carbon atoms of the naphthopyran compound. The number 6 carbon atom of the naphthopyran compound has a hydrogen substituent.

The foregoing described naphthopyran compounds may be represented by the following graphic formula I in which the numbers 1 through 10 identify the ring atoms of the naphthopyran.

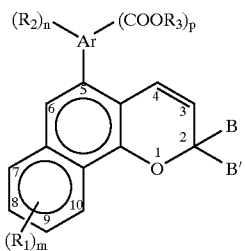

Ar in graphic formula I may be selected from the group consisting of:
(i) an aryl group consisting of phenyl and naphthyl; and
(ii) an aromatic group consisting of furanyl, benzofuran-2-yl, benzofuran-3-yl, thienyl, benzothien-2-yl, benzothien-3-yl, dibenzofuran-4-yl, and dibenzothien-4-yl. Preferably, Ar is phenyl or thienyl.

In graphic formula I, each $R_1$ may be $C_1$–$C_6$ alkyl, $C_1$–$C_6$ alkoxy, or halogen, said halogen being bromo, chloro, fluoro or iodo and m is the integer 0, 1, 2 or 3. In one contemplated embodiment, each $R_1$ is $C_1$–$C_4$ alkyl, $C_1$–$C_4$ alkoxy, chloro or fluoro, and m is the integer 0, 1 or 2. In another contemplated embodiment, each $R_1$ is $C_1$–$C_3$ alkyl or $C_1$–$C_3$ alkoxy, and m is the integer 0 or 1.

Each $R_2$ in graphic formula I may be selected from the group consisting of aryl, i.e., phenyl and naphthyl, mono($C_1$–$C_6$)alkoxyaryl, di($C_1$–$C_6$)alkoxyaryl, mono($C_1$–$C_6$)alkylaryl, di($C_1$–$C_6$)alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di($C_1$–$C_6$)alkylaryl($C_1$–$C_6$)alkyl, mono- and di($C_1$–$C_6$)alkoxyaryl($C_1$–$C_6$)alkyl, mono- and di($C_1$–$C_6$)alkylaryl($C_1$–$C_6$)alkoxy, mono- and di($C_1$–$C_6$)alkoxyaryl ($C_1$–$C_6$)alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, and halogen, said halogen being bromo, chloro, fluoro or iodo, and n is the integer 0, 1, 2, or 3. In one contemplated embodiment, each $R_2$ is selected from the group consisting of aryl, aryloxy, aryl ($C_1$–$C_3$)alkyl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$) alkyl, fluoro and chloro and n is the integer 0, 1 or 2. In another contemplated embodiment, each $R_2$ is selected from the group consisting of $C_1$–$C_3$ alkyl, $C_1$–$C_3$ alkoxy, aryl, fluoro and chloro and n is the integer 0 or 1.

$R_3$ in graphic formula I may be $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono($C_1$–$C_4$)alkoxy($C_2$–$C_3$) alkyl, or $C_1$–$C_4$ haloalkyl, and p is the integer 0, 1 or 2, provided that the sum of n and p is less than or equal to 3 and when p is 2, n is 0. In one contemplated embodiment, $R_3$ is $C_1$–$C_3$ alkyl and p is the integer 0 or 1. In another contemplated embodiment, the ester group containing $R_3$ is ortho to the atom of the Ar group linked to the number 5 carbon atom of the naphtho portion of the naphthopyran.

B and B' in graphic formula I may each be selected from the group consisting of:
(i) an unsubstituted, mono-, di- and tri-substituted aryl group consisting of phenyl and naphthyl;
(ii) an unsubstituted, mono- and di-substituted heteroaromatic group consisting of pyridyl, furanyl, benzofuran-2-yl, benzofuran-3-yl, thienyl, benzothien-2-yl, benzothien-3-yl, dibenzofuran-4-yl, dibenzothien-4-yl, and carbazol-4-yl, each of said aryl and heteroaromatic substituents in parts (i) and (ii) being selected from the group consisting of hydroxy, aryl, mono($C_1$–$C_6$) alkoxyaryl, di($C_1$–$C_6$)alkoxyaryl, mono($C_1$–$C_6$) alkylaryl, di($C_1$–$C_6$)alkylaryl, haloaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di($C_1$–$C_6$)alkylaryl ($C_1$–$C_6$)alkyl, mono- and di($C_1$–$C_6$)alkoxyaryl($C_1$–$C_6$) alkyl, mono- and di($C_1$–$C_6$)alkylaryl($C_1$–$C_6$)alkoxy, mono- and di($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ haloalkyl, $C_1$–$C_6$ alkoxy, mono ($C_1$–$C_6$)alkoxy($C_1$–$C_4$)alkyl, acryloxy, methacryloxy and halogen, said halogen and halo being bromo, chloro, fluoro or iodo;
(iii) the group represented by graphic formula IIA or IIB:

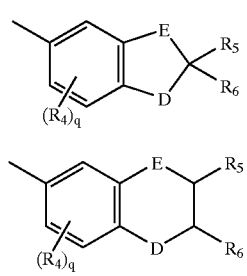

wherein E may be methylene or oxygen and D may be oxygen or substituted nitrogen, provided that when D is substituted nitrogen, E is methylene, said nitrogen substituents being selected from the group consisting of hydrogen, $C_1$–$C_6$ alkyl and $C_2$–$C_6$ acyl; each $R_4$ is $C_1$–$C_6$ alkyl, $C_1$–$C_6$ alkoxy, hydroxy, or halogen, said halogen being bromo, chloro, fluoro or iodo; $R_5$ and $R_6$ are each hydrogen or $C_1$–$C_6$ alkyl; and q is the integer 0, 1 or 2;
(iv) $C_1$–$C_6$ alkyl, $C_1$–$C_6$ haloalkyl, $C_1$–$C_6$ alkoxy($C_1$–$C_4$) alkyl; and
(v) the group represented by the following graphic formula:

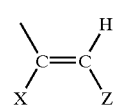

wherein X in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, or halogen.

In one contemplated embodiment, B and B' are each selected from the group consisting of: (i) phenyl, mono-substituted phenyl and di-substituted phenyl, preferably substituted in the meta and/or para positions; (ii) the unsubstituted, mono- and di-substituted heteroaromatic groups furanyl, benzofuran-2-yl, thienyl, benzothien-2-yl, dibenzofuran-2-yl and dibenzothien-2-yl, each of said phenyl and heteroaromatic substituents in (i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIA and IIB, wherein E is methylene and D is oxygen, $R_4$ is $C_1$–$C_3$ alkyl or $C_1$–$C_3$ alkoxy, $R_5$ and $R_6$ are each hydrogen or $C_1$–$C_4$ alkyl; and q is the integer 0 or 1; (iv) $C_1$–$C_4$ alkyl; and (v) the group represented by the graphic formula IIC wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro.

In another contemplated embodiment, B and B' are each selected from the group consisting of (i) phenyl, mono-and di-substituted phenyl; (ii) the unsubstituted, mono- and di-substituted heteroaromatic groups furanyl, benzofuran-2-yl, thienyl and benzothien-2-yl, each of said phenyl and heteroaromatic substituents in (i) and (ii) being selected from the group consisting of hydroxy, $C_1$–$C_3$ alkyl, $C_1$–$C_3$ alkoxy, aryl, indolino, fluoro and chloro; and (iii) the group represented by graphic formula IIA, wherein E is carbon and D is oxygen, $R_4$ is $C_1$–$C_3$ alkyl or $C_1$–$C_3$ alkoxy, $R_5$ and $R_6$ are each hydrogen or $C_1$–$C_3$ alkyl, and q is the integer 0 or 1.

Compounds represented by graphic formula I may be prepared by the following described Reactions A through D. Compounds represented by graphic formula V or VA are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions,* George A. Olah, Interscience Publishers, 1964, Vol. 3, Chapter XXXI (Aromatic Ketone Synthesis), and *"Regioselective Friedel-Crafts Acylation of* 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent possible substituents, as described hereinbefore with respect to graphic formula I.

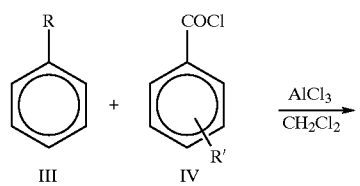

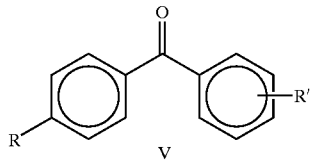

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

Reaction B

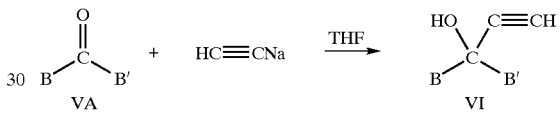

In Reaction C, the compounds represented by graphic formulae VII and VIII are first reacted at elevated temperatures and then further reacted in the presence of a base such as potassium hydroxide to form the corresponding substituted naphthol represented by graphic formula IX. Compounds VII and VIII may each be purchased. Alternatively, compound VIII may be prepared by the method described by T. Sakamoto et al., *Synthesis,* pages 312–314 (1983) and by S. Takahashi et al., *Synthesis,* pages 627–630 (1980). Synthesis of phenyl naphthols are further described in C. Kipping et al., J. Pralet. Chem., Vol. 315, pages 887–894 (1973) and J. Bao et al., J. Amer. Chem. Soc., Vol. 118, pages 3392–3405 (1996).

Reaction C

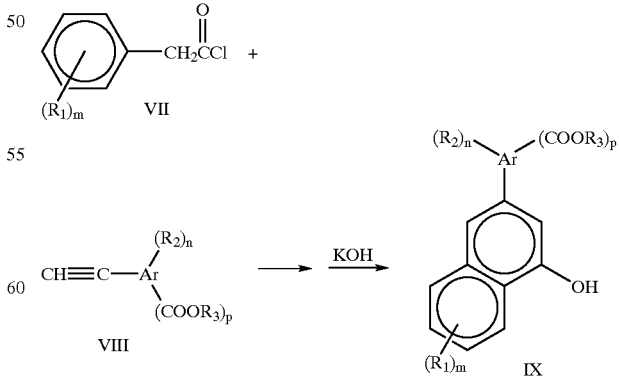

In Reaction D, the propargyl alcohol represented by graphic formula VI is coupled with the naphthol represented by graphic formula IX in the presence of an acid such as p-toluene sulfonic acid (PTSA) and in a suitable solvent such as toluene to form compounds represented by graphic formula I.

Reaction D

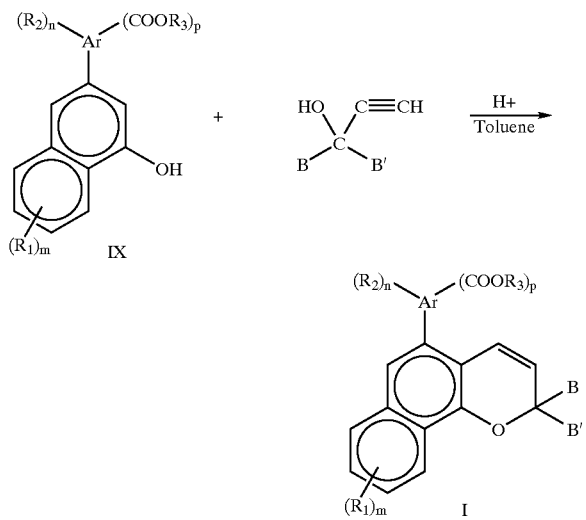

Compounds represented by graphic formula I may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. As used herein, coating compositions are defined herein to include polymeric coating compositions prepared from materials such as polyurethanes, epoxy resins and other resins used to produce synthetic polymers; paints, i.e., a pigmented liquid or paste used for the decoration, protection and/or the identification of a substrate; and inks, i.e., a pigmented liquid or paste used for writing and printing on substrates Potential substrates for coating compositions containing the compounds of the present invention include paper, glass, ceramics, wood, masonry, textiles, metals and polymeric organic materials.

Coating compositions may be used to produce polymeric coatings on optical elements, verification marks on security documents, e.g., documents such as banknotes, passport and drivers' licenses, for which authentication or verification of authenticity may be desired. The 5-aromatic substituted naphthopyrans represented by graphic formula I exhibit color changes from colorless to colors ranging from yellow to orange.

Examples of naphthopyrans and contemplated naphthopyran compounds that have or are expected to have desirable photochromic properties and are within the scope of the invention include the following:

(a) 2,2-diphenyl-5-(2-methoxycarbonylphenyl)-2H-naphtho[1, 2-b]pyran;
(b) 2,2-diphenyl-5-(4-methoxycarbonylphenyl)-2H-naphtho[1,2-b]pyran;
(c) 2,2-diphenyl-5-(thien-2-yl)-2H-naphtho[1,2-b]pyran;
(d) 2,2-diphenyl-5-(phenyl)-2H-naphtho[1,2-b]pyran;
(e) 2-phenyl, 2-(4-methoxyphenyl)-5-phenyl-2H-naphtho[1,2-b]pyran;
(f) 2,2-di(4-methoxyphenyl)-5-phenyl-2H-naphtho[1,2-b]pyran;
(g) 2-phenyl, 2-(4-morpholinophenyl)-5-phenyl-2H-naphtho[1,2-b]pyran;
(h) 2,2-di(4-methoxyphenyl)-9-methoxy-5-phenyl-2H-naphtho[1,2-b]pyran;
(i) 2-phenyl, 2-(4-morpholinophenyl)-9-methoxy-5-phenyl-2H- naphtho[1,2-b]pyran;
(j) 2,2-di(4-methoxyphenyl)-5-(4-methylphenyl)-2H-naphtho[1,2-b]pyran;
(k) 2-phenyl, 2-(4-methoxyphenyl)-5(4-methylphenyl)-2H-naphtho[1,2-b]pyran; and
(l) 2,2-di(4-methoxyphenyl)-9-methoxy-5-(4-methylphenyl)-2H-naphtho[1,2-b]pyran.

Other than where otherwise indicated, all numbers expressing wavelengths, quantities of ingredients or reaction conditions used herein are to be understood as modified in all instances by the term "about".

The disclosures of the patents and articles cited herein describing procedures for making the compounds of the present invention, complementary photochromic compounds, polymeric coatings and methods of applying such coatings, polymeric organic host materials and polymerizates are incorporated herein, in toto, by reference.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

The complementary organic photochromic compounds may include other naphthopyrans, benzopyrans, indenonaphthopyrans, oxazines, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro( indoline)naphthoxazines, spiro(indoline)pyridobenzoxazines, spiro(benzindoline) pyridobenzoxazines, spiro(benzindoline)naphthoxazines, spiro(indoline)benzoxazines, mercury dithizonates, fulgides, fulgimides and mixtures of such photochromic compounds. Many of such photochromic compounds are described in the open literature, e.g., U.S. Pat. Nos. 5,645,767 and 6,153,126.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of photochromic substance or composition containing same applied to or incorporated into a coating composition or a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 2.0, e.g., from 0.2 to 1.0, milligrams per square centimeter of surface to which the photochromic substance (s) is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions or dispersions of the photochromic compounds may be used to incorporate the photochromic compounds into a polymeric organic host material or other materials such as textiles and coating compositions. Coating compositions may be applied to the substrate using a coating process such as that described in U.S. Pat. 3,971,872.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The polymeric coating composition includes compositions resulting in thermoplastic or thermosetting coatings, which are described in the *Kirk-Othmer Encyclopedia of Chemical Technology,* Fourth Edition, Volume 6, pages 669 to 760. The coating may comprise at least one, polymer selected from the group consisting of polyurethanes, melamine resins, polyvinyl alcohol, polyacrylates, polymethacrylates, polyamide resins and epoxy resins. Such polymer-forming coating compositions are described in U.S. Pat. No. 4,425,403.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, mono- or polyfunctional, e.g., di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic naphthopyrans of the present invention with optical organic resin monomers used to produce optically clear coatings and polymerizates, i.e., materials suitable for optical applications, such as for example plano and ophthalmic lenses, windows, and automotive transparencies. Such optically clear polymerizates may have a refractive index that may range from 1.48 to 1.75, e.g., from 1.495 to 1.66.

Specifically contemplated are polymerizates of optical resins sold by PPG Industries, Inc. under the CR-designation, e.g., CR-307, CR-407 and CR-607, and polymerizates prepared for use as hard or soft contact lenses. Methods for producing both types of contact lenses are disclosed in U.S. Pat. No. 5,166,345, column 11, line 52, to column 12, line 52. Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631.

The present invention is more particularly described in the following examples, which are intended as illustrative only, since numerous modifications and variations therein will be apparent to those skilled in the art.

EXAMPLE 1

Step 1

Phenyl acetyl chloride (20 milliliters (mL)) and phenyl acetylene (10 mL) were mixed in a reaction flask equipped with a magnetic stirrer, oil bath and a condenser. The mixture was maintained at a temperature of 180° C. and stirred overnight. After cooling to room temperature, potassium hydroxide (5 grams), water (10 mL) and methanol (200 mL) were added to the reaction flask and the reaction mixture was stirred overnight at room temperature. The methanol was removed under vacuum and the remaining black residue was dissolved in a 10 weight percent solution of potassium hydroxide (150 mL). The resulting solution was extracted with ether three times. The remaining aqueous portion was acidified and extracted with ether three times. The ether extracts were combined, washed with sodium bicarbonate solution three times and dried over anhydrous sodium sulfate. The solvent, methanol, was removed on a rotary evaporator to yield 11.0 grams of product which crystallized at room temperature. A nuclear magnetic resonance (NMR) spectrum showed the product to have a structure consistent with 3-phenyl-1-naphthol.

Step 2

3-Phenyl-1-naphthol (4.4 grams) from Step 1, 1,1-diphenylpropargyl alcohol (4.6 grams), p-toluene sulfonic acid (0.2 gram) and toluene (100 mL) were mixed in a reaction flask and stirred for one hour at room temperature. The reaction mixture was heated to 50–60° C. and stirred for another two hours. The resulting mixture was washed with water twice and dried over anhydrous sodium sulfate. The solvent, toluene, was removed using a rotary evaporator. The resulting product was purified on a silica gel column (using hexane as the eluant) to yield 3.7 grams of a crystalline product having a melting point of 150–151° C. An NMR spectrum showed the product to have a structure consistent with 2,2-diphenyl-5-phenyl-2H-naphtho[1,2-b]pyran.

EXAMPLE 2

The procedure of Example 1 was followed except that in Step 2, 1-phenyl, 1-(4-methoxyphenyl)-propargyl alcohol was used instead of 1,1-diphenyl-propargyl alcohol. NMR analysis showed the product to have a structure consistent with 2-phenyl, 2-(4-methoxyphenyl)-5-phenyl-2H-naphtho[1,2-b]pyran.

EXAMPLE 3

The procedure of Example 1 was followed except that in Step 2, 1,1-di(4-methoxyphenyl)-propargyl alcohol was used instead of 1,1-diphenyl-propargyl alcohol. NMR analysis showed the product to have a structure consistent with 2,2-di(4-methoxyphenyl)-5-phenyl-2H-naphtho[1,2-b]pyran.

EXAMPLE 4

The procedure of Example 1 was followed except that in Step 2, 1-phenyl, 1-(4-morpholinophenyl)-propargyl alcohol was used instead of 1,1-diphenyl-propargyl alcohol. NMR analysis showed the product to have a structure consistent with 2-phenyl, 2-(4-morpholinophenyl)-5-phenyl-2H-naphtho[1,2-b]pyran.

EXAMPLE 5

Step 1

The procedure of Step 1 of Example 1 was followed except that: 4-methoxy phenyl acetyl chloride was used in place of phenyl acetyl chloride. The resulting mixture containing 7-methoxy-3-phenyl-1-naphthol was used in the next step without further purification.

Step 2

The procedure of Step 2 of Example 1 was followed except that: 7-methoxy-3-phenyl-1-naphthol and 1,1-di(4-methoxyphenyl)-propargyl alcohol were used in place of 1,1-di phenyl-propargyl alcohol. NMR analysis showed the product to have a structure consistent with 2,2-di(4-methoxyphenyl)-9-methoxy-5-phenyl-2H-naphtho[1,2-b]pyran.

EXAMPLE 6

The procedure Example 5 was followed except that in Step 2, 1-phenyl, 1-(4-morpholinophenyl)-propargyl alcohol was used in place of 1,1-di(4-methoxyphenyl)-propargyl alcohol. NMR analysis showed the product to have a structure consistent with 2-phenyl, 2-(4-morpholinophenyl)-9-methoxy-5-phenyl-2H-naphtho[1,2-b]pyran.

EXAMPLE 7

Step 1

The procedure of Step 1 of Example 1 was followed except that 4-ethynyl toluene was used in place of phenyl acetylene. The resulting mixture containing 3-(4-methylphenyl)-1-naphthol was used in the next step without further purification.

Step 2

The procedure of Step 2 of Example 1 was followed except that 3-(4-methylphenyl)-1-naphthol and 1,1-di(4-methoxyphenyl)-propargyl alcohol were used. NMR analysis showed the product to have a structure consistent with 2,2-di(4-methoxyphenyl)-5-(4-methylphenyl)-2H-naphtho[1,2-b]pyran.

EXAMPLE 8

The procedure of Example 7 was followed except that in Step 2, 1-phenyl, 1-(4-methoxyphenyl)-propargyl alcohol was used in place of 1,1-di(4-methoxyphenyl)-propargyl alcohol. NMR analysis showed the product to have a structure consistent with 2-phenyl, 2-(4-methoxyphenyl)-5-(4-methylphenyl)-2H-naphtho[1,2-b]pyran.

EXAMPLE 9

Step 1

The procedure of Step 1 of Example 1 was followed except that 4-methoxy phenyl acetyl chloride was used in place of phenyl acetyl chloride and 4-ethynyl toluene was used in place of phenyl acetylene. The resulting mixture containing 3-(4-methylphenyl)-7-methoxy-1-naphthol was used in the next step without further purification.

Step 2

The procedure of Step 2 of Example 1 was followed except that 3-(4-methylphenyl)-7-methoxy-3-phenyl-1-naphthol and 1,1-di(4-methoxyphenyl)-propargyl alcohol were used. NMR analysis showed the product to have a structure consistent with 2,2-di(4-methoxyphenyl)-9-methoxy-5-(4-methylphenyl)-2H-naphtho[1,2-b]pyran.

Comparative Examples 1–3

Comparative Example 1 was prepared according to the procedures for preparing Comparative Example 1 in U.S. Pat. No. 5,458,814, column 18, lines 1–8. The compound was determined to be 2,2-diphenyl-[2H]naphtho[1,2-b]pyran.

Comparative Example 2 was produced following the procedures of Step 2 of Example 1 of U.S. Pat. No. 5,458,814, except that 1-hydroxynaphthylene was used in place of methyl-1,4-dihydroxy-2-naphthoate to produce 2,2-di(4-methoxyphenyl)-[2H]naphtho[1,2-b]pyran.

Comparative Example 3 was prepared according to the procedures for preparing Example 2 in U.S. Pat. No. 5,658,501. The compound was determined to be 2,2-di(4-methoxyphenyl)-5-(2,4-dimethoxyphenyl)-6-acetoxy-[2H]naphtho[1,2-b]pyron.

EXAMPLE 10

Part A

Testing was done with the photochromic compounds described in Examples 1 through 9 and Comparative Examples 1 through 3 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm2). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (AOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where %Ta is the percent transmittance in the activated state and the logarithm is to the base 10.

The optical properties of the photochromic compounds in the test squares are reported in Table 1. The ΔOD/Min, which represents the sensitivity of the photochromic compound's response to UV light, was measured over the first five (5) seconds of UV exposure, then expressed on a per minute basis. The saturation optical density (ΔOD@ Saturation) was taken under identical conditions as the ΔOD/Min, except UV exposure was continued for 15 minutes.

The lambda max (Vis) is the wavelength in the visible spectrum at which the maximum absorption of the activated (colored) form of the photochromic compound in a test square occurs. The lambda max (Vis) wavelengths reported in Table 1 were determined by testing the photochromic test square polymerizates of Part A in a Varian Cary 3 uv-visible spectrophotometer. The bleach rate (T 1/2) is the time interval in seconds for the absorbance of the activated form of the photochromic compound in the test squares to read one half the highest absorbance at room temperature (72° F., 22.2° C.) after removal of the source of activating light.

Each of the compounds of the Examples and the Comparative Examples exhibited dual peak absorptions in the visible spectrum (lambda max visible) in distinct color regions. For the highest lambda max visible (Band B), the corresponding optical density (Δ OD/Min, and Δ OD at saturation), for the compounds of the Examples and Comparative Examples are tabulated in Table 1. Table 1 also includes the bleach rate (T 1/2) for each of the compounds as measured at Band B.

TABLE 1

| Compound Example | Sensitivity ΔOD/MIN | ΔOD @ Saturation | Bleach Rate T ½ sec | λ MAX (nm) Vis |
|---|---|---|---|---|
| 1 (Band A) | | | | 406 |
| 1 (Band B) | 0.12 | 0.27 | 120 | 489 |
| Comp. Ex. 1 (Band A) | | | | 403 |
| Comp. Ex. 1 (Band B) | 0.11 | 0.85 | >1200 | 480 |
| 2 (Band A) | | | | 419 |
| 2 (Band B) | 0.12 | 0.18 | 71 | 500 |
| 3 (Band A) | | | | 424 |
| 3 (Band B) | 0.13 | 0.11 | 50 | 510 |
| 4 (Band A) | | | | 448 |
| 4 (Band B) | 0.13 | 0.15 | 72 | 538 |
| 5 (Band A) | | | | 436 |
| 5 (Band B) | 0.10 | 0.10 | 56 | 538 |
| 6 (Band A) | | | | 482 |
| 6 (Band B) | 0.12 | 0.17 | 78 | 553 |
| 7 (Band A) | | | | 425 |
| 7 (Band B) | 0.10 | 0.11 | 52 | 511 |
| 8 (Band B) | | | | 419 |
| 8 (Band B) | 0.16 | 0.18 | 73 | 501 |
| 9 (Band B) | | | | 436 |
| 9 (Band B) | 0.09 | 0.12 | 56 | 539 |
| Comp. Ex. 2 (Band A) | | | | 417 |
| Comp. Ex. 2 (Band B) | 0.14 | 0.59 | 377 | 507 |
| Comp. Ex. 3 (Band A) | | | | 422 |
| Comp. Ex. 3 (Band B) | 0.15 | 0.55 | 248 | 511 |

The results of Table 1 show that the compounds of the present invention demonstrate a range of photochromic properties, e.g., lambda max values for Band A from 406 to 482 nanometers and for Band B from 489 to 553 nanometers, sensitivity levels from 0.09 to 0.16, values for ΔOD ® Saturation from 0.10 to 0.27 and Bleach Rates from 50 to 120 seconds. Comparative Example 1 is an unsubstituted naphthopyran that has comparable lambda max values and sensitivities to Example 1, except that the bleach rate of Example 1 is ten times faster. Comparative Examples 2 and 3 have methoxy substituents on the phenyl at the 2 position. Comparative Example 3 also has a dimethoxy substituent at position 5 and an acetoxy substituent at position 6. A comparison between Comparative Examples 2 and 3 and Example 3, 5 and 7 show that in each case, the compounds of the present invention fade faster than the comparative examples.

The present invention has been described with reference to specific details of particular embodiments thereof. It is not intended that such details be regarded as limitations upon the scope of the invention except insofar as to the extent that they are included in the accompanying claims.

I claim:
1. A naphthopyran of 2H-naphtho[1,2-b]pyran structure, characterized by having in the 5 position, a group, —Ar(R$_2$)$_n$(COOR$_3$)$_p$, wherein:
  (a) Ar is selected from the group consisting of:
    (i) an aryl group consisting of phenyl and naphthyl; and
    (ii) an aromatic group consisting of furanyl, benzofuran-2-yl, benzofuran-3-yl, thienyl, benzothien-2-yl, benzothien-3-yl, dibenzofuranyl, dibenzothienyl and fluorenyl;
  (b) each R$_2$ is selected from the group consisting of aryl, mono(C$_1$–C$_6$)alkoxyaryl, di(C$_1$–C$_6$)alkoxyaryl, mono (C$_1$–C$_6$)alkylaryl, di(C$_1$–C$_6$)alkylaryl, haloaryl, C$_3$–C$_7$ cycloalkylaryl, C$_3$–C$_7$ cycloalkyl, C$_3$–C$_7$ cycloalkyloxy, C$_3$–C$_7$ cycloalkyloxy(C$_1$–C$_6$)alkyl, C$_3$–C$_7$ cycloalkyloxy(C$_1$–C$_6$)alkoxy, aryl(C$_1$–C$_6$)alkyl, aryl(C$_1$–C$_6$)alkoxy, aryloxy, aryloxy(C$_1$–C$_6$)alkyl, aryloxy(C$_1$–C$_6$)alkoxy, mono- and di(C$_1$–C$_6$)alkylaryl (C$_1$–C$_6$)alkyl, mono- and di(C$_1$–C$_6$)alkoxyaryl(C$_1$–C$_6$) alkyl, mono- and di(C$_1$–C$_6$)alkylaryl(C$_1$–C$_6$)alkoxy, mono- and di(C$_1$–C$_6$)alkoxyaryl(C$_1$–C$_6$)alkyl, mono- and di(C$_1$–C$_6$)alkoxyaryl(C$_1$–C$_6$)alkoxy, C$_1$–C$_6$ alkyl, C$_1$–C$_6$ bromoalkyl, C$_1$–C$_6$ chloroalkyl, C$_1$–C$_6$ fluoroalkyl, C$_1$–C$_6$ alkoxy, mono(C$_1$–C$_6$)alkoxy (C$_1$–C$_4$)alkyl, and halogen, said halo and halogen being bromo, chloro, fluoro or iodo, and n is the integer 0, 1, 2, or 3; and
  (c) each R$_3$ is selected from the group consisting of C$_1$–C$_4$ alkyl, phenyl, mono(C$_1$–C$_4$)alkyl substituted phenyl, mono(C$_1$–C$_4$)alkoxy substituted phenyl, phenyl (C$_1$–C$_2$)alkyl, mono(C$_1$–C$_4$)alkyl substituted phenyl (C$_1$–C$_2$)alkyl, mono(C$_1$–C$_4$)alkoxy substituted phenyl (C$_1$–C$_2$)alkyl, mono(C$_1$–C$_4$)alkoxy(C$_2$–C$_3$)alkyl, and C$_1$–C$_4$ haloalkyl, and p is the integer 0, 1 or 2, the sum of n and p being 0, 1, 2 or 3 and wherein when p is 2, n is 0.

2. The naphthopyran compound of claim 1 wherein said naphthopyran is represented by the following graphic formula:

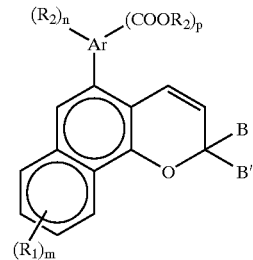

wherein,
  (a) Ar is selected from the group consisting of:
    (i) an aryl group consisting of phenyl and naphthyl; and
    (ii) an aromatic group consisting of furanyl, benzofuran-2-yl, benzofuran-3-yl, thienyl, benzothien-2-yl, benzothien-3-yl, dibenzofuranyl, dibenzothienyl and fluorenyl;
  (b) each R$_1$ is C$_1$–C$_6$ alkyl, C$_1$–C$_6$ alkoxy, or halogen and m is the integer 0, 1, 2 or 3;
  (c) each R$_2$ is selected from the group consisting of aryl, mono(C$_1$–C$_6$)alkoxyaryl, di(C$_1$–C$_6$)alkoxyaryl, mono (C$_1$–C$_6$)alkylaryl, di(C$_1$–C$_6$)alkylaryl, haloaryl, C$_3$–C$_7$ cycloalkylaryl, C$_3$–C$_7$ cycloalkyl, C$_3$–C$_7$ cycloalkyloxy, C$_3$–C$_7$ cycloalkyloxy(C$_1$–C$_6$)alkyl, C$_3$–C$_7$ cycloalkyloxy(C$_1$–C$_6$)alkoxy, aryl(C$_1$–C$_6$)alkyl, aryl(C$_1$–C$_6$)alkoxy, aryloxy, aryloxy(C$_1$–C$_6$)alkyl, aryloxy($C_1$–$C_6$)alkoxy, mono- and di($C_1$–$C_6$)alkylaryl($C_1$–$C_6$)alkyl, mono- and di($C_1$–$C_6$)alkoxyaryl($C_1$–$C_6$)alkyl, mono- and di($C_1$–$C_6$)alkylaryl($C_1$–$C_6$)alkoxy, mono- and di($C_1$–$C_6$)alkoxyaryl($C_1$–$C_6$)alkoxy, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, bromo, chloro and fluoro and n is the integer 0, 1, 2, or 3;

(d) $R_3$ is selected from the group consisting of $C_1$–$C_4$ alkyl, phenyl, mono($C_1$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono($C_1$–$C_4$)alkoxy($C_2$–$C_3$)alkyl, and $C_1$–$C_4$ haloalkyl, and p is the integer 0, 1 or 2, the sum of n and p being 0, 1, 2 or 3 and wherein when p is 2, n is 0; and (e) B and B' are each selected from the group consisting of:
  (i) an unsubstituted, mono-, di- and tri-substituted aryl group consisting of phenyl and naphthyl;
  (ii) an unsubstituted, mono- and di-substituted heteroaromatic group consisting of pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (e)(i) and (ii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro;
  (iii) the group represented by one of the following graphic formulae:

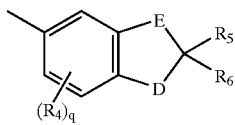 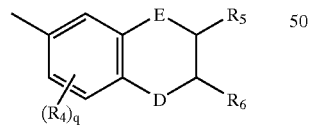

wherein E is methylene or oxygen and D is oxygen or substituted nitrogen, provided that when D is substituted nitrogen, E is methylene, said nitrogen substituents being selected from the group consisting of hydrogen, $C_1$–$C_6$ alkyl and $C_2$–$C_6$ acyl; each $R_4$ is $C_1$–$C_6$ alkyl, $C_1$–$C_6$ alkoxy, hydroxy, bromo, chloro or fluoro; $R_5$ and $R_6$ are each hydrogen or $C_1$–$C_6$ alkyl; and q is the integer 0, 1 or 2;
  (iv) $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy($C_1$–$C_4$)alkyl; and
  (v) the group represented by the following graphic formula:

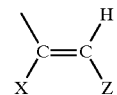

wherein X is hydrogen or $C_1$–$C_4$ alkyl and Z is selected from an unsubstituted, mono-, and di-substituted members of the group consisting of naphthyl, phenyl, furanyl and thienyl, each of said group substituents being $C_1$–$C_4$ alkyl, $C_1$–$C_4$ alkoxy, bromo, fluoro or chloro.

3. The naphthopyran of claim 2 wherein,
(a) each $R_1$ is $C_1$–$C_4$ alkyl, $C_1$–$C_4$ alkoxy, chloro or fluoro, and m is the integer 0, 1 or 2;
(b) Ar is phenyl or thienyl;
(c) each $R_2$ is selected from the group consisting of aryl, aryloxy, aryl($C_1$–$C_3$)alkyl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro and n is the integer 0, 1 or 2;
(d) $R_3$ is $C_1$–$C_3$ alkyl and p is the integer 0 or 1, wherein when p is 1, n is 0; and
(e) B and B' are each selected from the group consisting of:
  (i) phenyl, mono-substituted phenyl and di-substituted phenyl;
  (ii) an unsubstituted, mono-substituted and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (e)(i) and (ii) being selected from the group consisting of hydroxy, aryl, aryloxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;
  (iii) the group represented by one of the following graphic formula:

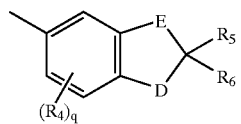 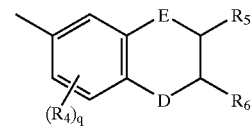

wherein E is methylene and D is oxygen, $R_4$ is $C_1$–$C_3$ alkyl or $C_1$–$C_3$ alkoxy, $R_5$ and $R_6$ are each hydrogen or $C_1$–$C_4$ alkyl; and q is the integer 0 or 1;
  (iv) $C_1$–$C_4$ alkyl; and
  (v) the group represented by the following graphic formula:

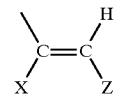

wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro.

4. The naphthopyran of claim 3 wherein:
(a) $R_1$ is $C_1$–$C_3$ alkyl or $C_1$–$C_3$ alkoxy, and m is the integer 0 or 1;
(b) Ar is phenyl or thienyl;
(c) $R_2$ is $C_1$–$C_3$ alkyl, $C_1$–$C_3$ alkoxy, aryl, fluoro and chloro, and n is the integer 0 or 1;
(d) $R_3$ is $C_1$–$C_3$ alkyl and p is the integer 0 or 1, wherein when p is 1, n is 0; and
(e) B and B' are each selected from the group consisting of:
  (i) phenyl, mono-substituted and di-substituted phenyl;
  (ii) an unsubstituted, mono-, and di-substituted heteroaromatic groups furanyl, benzofuran-2-yl, thienyl and benzothien-2-yl, each of said phenyl and heteroaromatic substituents in (e)(i) and (ii) being selected from the group consisting of hydroxy, $C_1$–$C_3$ alkyl, $C_1$–$C_3$ alkoxy, aryl, indolino, fluoro and chloro; and
  (iii) the group represented by the following graphic formula:

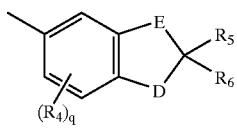

wherein E is methylene and D is oxygen, $R_4$ is $C_1$–$C_3$ alkyl or $C_1$–$C_3$ alkoxy, $R_5$ and $R_6$ are each hydrogen or $C_1$–$C_3$ alkyl, and q is the integer 0 or 1.

5. A naphthopyran compound selected from the group consisting of:

(a) 2,2-diphenyl-5-(2-methoxycarbonylphenyl)-2H-naphtho[1,2-b]pyran;
(b) 2,2-diphenyl-5-(4-methoxycarbonylphenyl)-2H-naphtho[1,2-b]pyran;
(c) 2,2-diphenyl-5-(thien-2-yl)-2H-naphtho[1,2-b]pyran;
(d) 2,2-diphenyl-5-(phenyl)-2H-naphtho[1,2-b]pyran;.
(e) 2-phenyl, 2-(4-methoxyphenyl)-5-phenyl-2H-naphtho[1,2-b]pyran;
(f) 2,2-di(4-methoxyphenyl)-5-phenyl-2H-naphtho[1,2-b]pyran;
(g) 2-phenyl, 2-(4-morpholinophenyl)-5-phenyl-2H-naphtho[1,2-b]pyran;
(h) 2,2-di(4-methoxyphenyl)-9-methoxy-5-phenyl-2H-naphtho[1,2-b]pyran;
(i) 2-phenyl, 2-(4-morpholinophenyl)-9-methoxy-5-phenyl-2H-naphtho[1,2-b]pyran;
(j) 2,2-di(4-methoxyphenyl)-5-(4-methylphenyl)-2H-naphtho[1,2-b]pyran;
(k) 2-phenyl, 2-(4-methoxyphenyl)-5-(4-methylphenyl)-2H-naphtho[1,2-b]pyran; and
(l) 2,2-di(4-methoxyphenyl)-9-methoxy-5-(4-methylphenyl)-2H-naphtho[1,2-b]pyran.

6. A photochromic article comprising a polymeric organic host material and a photochromic amount of the naphthopyran compound of claim 1.

7. The photochromic article of claim 6 wherein the polymeric organic host material is selected from the group consisting of polyacrylates, polymethacrylates, poly($C_1$–$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

8. The photochromic article of claim 6 wherein the naphthopyran compound is present in an amount of from 0.05 to 2.0 milligram per square centimeter of polymeric organic host material surface to which the photochromic substance(s) is incorporated or applied.

9. The photochromic article of claim 6 wherein said polymeric organic host material is an optical element.

10. The photochromic article of claim 9 wherein said optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 2.

12. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 4.

13. A photochromic article comprising, in combination, a solid substrate and a photochromic amount of each of (a) at least one naphthopyran compound of claim 1, and (b) at least one other organic photochromic compound having at least one activated absorption maxima within the range of between 400 and 700 nanometers.

14. A photochromic article comprising a polymerizate of an optical organic resin monomer and a photochromic amount of the naphthopyran compound of claim 1.

15. The photochromic article of claim 14 wherein the refractive index of the polymerizate is from about 1.48 to about 1.75.

16. The photochromic article of claim 14 wherein the polymerizate is an optical element.

17. The photochromic article of claim 16 wherein said optical element is a lens.

18. A photochromic article comprising, in combination, a solid substrate and on at least one surface thereof a cured coating of a coating composition having a photochromic amount of the naphthopyran compound of claim 1.

19. The photochromic article of claim 18 wherein said coating composition is selected from the group consisting of a polymeric coating composition, paint and ink.

20. The photochromic article of claim 18 wherein the substrate is selected from the group consisting of glass, masonry, textiles, ceramics, metals, wood, paper and polymeric organic materials.

21. A photochromic article comprising, in combination, a solid substrate and on at least one surface thereof a cured coating of a coating composition having a photochromic amount of the naphthopyran compound of claim 2.

22. A photochromic article comprising, in combination, a solid substrate and on at least one surface thereof a cured coating of a coating composition having a photochromic amount of the naphthopyran compound of claim 4.

* * * * *

UNITED STATES PATENT AND TRADEMARK OFFICE
CERTIFICATE OF CORRECTION

PATENT NO. : 6,478,989 B1
DATED : November 12, 2002
INVENTOR(S) : Jibing Lin

It is certified that error appears in the above-identified patent and that said Letters Patent is hereby corrected as shown below:

Column 16,
Line 40, delete graphic formula:

" 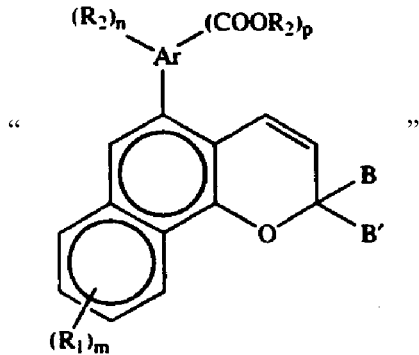 "

and insert:

-- 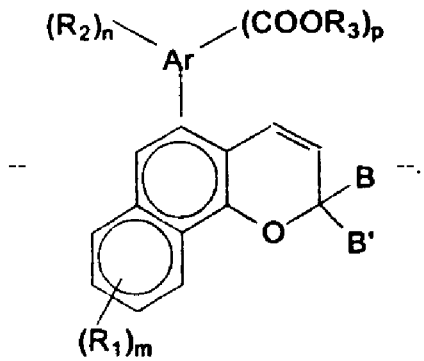 --.

Signed and Sealed this

Seventh Day of February, 2006

JON W. DUDAS
*Director of the United States Patent and Trademark Office*